United States Patent [19]

Tinti

[11] Patent Number: 4,600,794
[45] Date of Patent: Jul. 15, 1986

[54] PROCESS FOR PREPARING GAMMA-DIMETHYLAMINO L-BETA HYDROXY BUTYRIC ACID

[75] Inventor: Maria O. Tinti, Rome, Italy

[73] Assignee: Sigma Tau Industrie Farmaceutiche Riunite S.P.A., Rome, Italy

[21] Appl. No.: 750,690

[22] Filed: Jun. 28, 1985

[30] Foreign Application Priority Data

Jul. 27, 1984 [IT] Italy ................................ 48659 A/84

[51] Int. Cl.$^4$ ............................................ C07C 101/30
[52] U.S. Cl. .................................... 562/567; 560/170; 564/136; 564/197
[58] Field of Search ........................ 562/567; 560/170; 564/136, 197

[56] References Cited

U.S. PATENT DOCUMENTS 3,223,700  12/1965  Klauehn ............................... 564/197

FOREIGN PATENT DOCUMENTS 898396   3/1984  Belgium .
37-5172  6/1962  Japan ................................... 562/567
56-68649 6/1981  Japan ................................... 562/567

OTHER PUBLICATIONS

Keller, J. Med. Chem., 6 pp. 202–203 (1963).
Stokke, Biochim. Biophys Acta, 218 pp. 552–554 (1970).

*Primary Examiner*—Michael L. Shippen
*Attorney, Agent, or Firm*—Ladas & Parry

[57] ABSTRACT

Gamma dimethylamino L-beta hydroxy butyric acid (L-norcarnitine) is prepared by reacting gamma-iodo beta hydroxy butyric acid octyl ester with dimethylamine in a lower alkanol, e.g. ethanol, thereby obtaining a mixture of the hydroiodides of the gamma-dimethylamino L-beta hydroxy butyric acid ethyl ester and dimethylamide (in a molar ratio of about 60:40). The mixture is eluted on a weakly basic ion exchange resin activated in the OH− form in order to remove the iodide ions. Upon subsequent alkaline hydrolysis the desired compound is obtained.

1 Claim, No Drawings

PROCESS FOR PREPARING GAMMA-DIMETHYLAMINO L-BETA HYDROXY BUTYRIC ACID

The present invention relates to a process for preparing gamma-dimethylamino L-beta hydroxy butyric acid (L-norcarnitine), having the formula

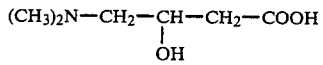
                                                    (I)

which clearly shows the structural relationship between (I) and L-carnitine.

Norcarnitine, in addition to being endowed per se with parmacological properties (see Keller at al, *J. Med. Chem.* 6, 202, 1963), is a versatile intermediate useful for preparing carnitine and carnitine alkanoyl derivatives (see e.g. the Japanese Pat. No. 303994, filed Dec. 24, 1959 in the name of Fujisawa Pharmaceutical Co.) which, as known, present several therapeutical utilizations.

There are already known some methods for synthesizing norcarnitine which present, however, several drawbacks which become particularly serious if an endeavour is made to carry them out on an industrial scale.

For instance, as taught in *Biochim. Biophys.* Acta 218, 552, (1970) and in *J. Label Compound Radiopharm* IX/4, 535, (1982), L-norcarnitine hydrochloride is synthesized as intermediate in the preparation of labelled L-carnitine. According to the method disclosed in these prior art references, L-norcarnitine is obtained in yields varying from 60 to 90% by demethylation of L-carnitine hydrochloride with sodium thiophenate.

It was found, however, that scaling up the process from laboratory to semi-pilot plant brings about a dramatic lowering of the yield down to values which are utterly unacceptable from an industrial stand point, while even at the semi-pilot plant scale serious problems originated by the sodium thiophenate toxicity are to be faced.

The object of the present invention is to provide a process for producing L-norcarnitine which does not present the drawbacks of the prior processes. In particular, via the process of the present invention good yields, even on an industrial scale, are achieved, while reactants entailing toxicity and pollution problems need not be utilized.

In accordance with the process of the present invention, L-norcarnitine is prepared via the following reaction scheme:

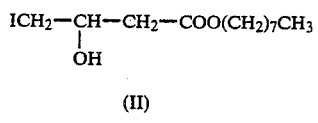
                                        (II)

octyl gamma iodo L-beta hydroxy butyrate

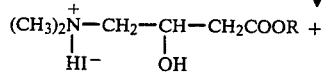

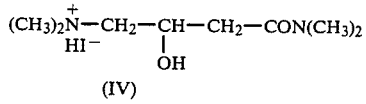

ester of the gamma dimethylamino L-beta hydroxy butyric acid, hydroiodide dimethyl amide of the gamma dimethylamino L-beta hydroxy butyric acid, hydroiodide

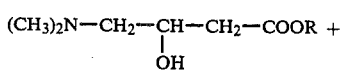
                                        (III')

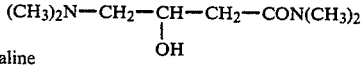
                                        (IV')

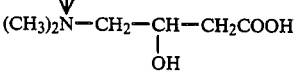
                                        (I)

gamma dimethylamino L-beta-hydroxy butyric acid (L-norarnitine)

(Compound (III') and (IV') are not isolated from the reaction mixture).

More specifically, the process is characterized by the following steps:

(a) reacting a solution of octyl gamma iodo L-beta hydroxy butyrate (II) in a lower alkanol ROH wherein R is lower alkyl with a solution of dimethylamine in the same lower alkanol with molar ratio from 1:2 to 1:4, keeping the reaction mixture under stirring at 25°–35° C. for 15–24 hours, thereby obtaining a mixture of the hydroiodides of the ester (III) and dimethylamide (IV) of the gamma-dimethylamino L-beta-hydroxy butyric acid;

(b) concentrating under vacuum the mixture of step (a), taking up with water the residue and purifying the mixture thus obtained by extraction with a water-immiscible organic solvent, eluting on a weakly basic ion exchange resin activated in the OH⁻ form in order to remove the iodide ions, thereby obtaining a mixture of ester (III') and dimethylamide (IV') of the gamma-dimethylamino L-beta-hydroxy-butyric acid which are not isolated;

(c) hydrolyzing the mixture of the ester (III') and amide (IV') in an alkaline aqueous environment at pH 11–13 at 40°–60° C. in about 4 to 8 hours thereby obtaining L-norcarnitine (I); and (d) purifyng the L-norcarnitine thus obtained by removal of the cations via elution on a weakly acid ion exchange resin activated in the H⁺ form.

The process for preparing the starting compound in the process of the present invention, namely octyl gamma iodo L-beta hydroxy butyrate (II), is disclosed e.g. in the Italian patent application No. 24018 A/83 filed Dec. 5, 1983 by the same applicants as the present patent application or in the corrisponding Belgian Pat. No. 898396.

The lower alkanol of step (a) is preferably ethanol.

The water-immiscible organic solvent of step (b) is preferably ethyl ether.

The weakly basic ion-exchange resin is preferably AMBERLITE IR 45.

The weakly acid ion-exchange resin is preferably AMBERLITE IR 50.

The following non-limiting example illustrates the process of the present invention.

EXAMPLE

Octyl gamma-iodo L-beta-hydroxy butyrate (3.42 g; 0.01 moles) diluted with EtOH was added to a 33% solution of dimethylamine in EtOH (5.05 g; 0.03. moles). The resulting mixture was kept under stirring for 24 hours and then concentrated to dryness under vacuum. The residue was then taken up with a little water and extracted 3 times with ethyl ether in order to remove the unreacted octyl gamma-iodo L-beta-hydroxy butyrate. The resulting aqueous solution was eluted on a weakly basic, AMBERLITE IR 45 ion-exchange resin activated in the OH⁻ form for removing the iodide ions.

The fractions at pH 10–11 were collected. The fractions were pooled and lyophilized and then checked via TLC (CHCl₃—MetOH-IsoprOH—H₂O—AcOH; 60-40-10-15-15-) $R_F$ 0.6–0.55. The NMR spectrum showed that the lyophilizate consisted of a mixture of about 60% ethyl gamma dimethylamino beta hydroxy butyrate and 40% gamma dimethylamino beta-hydroxy N,N-dimethyl butyramide.

NMR δ D₂O 4.8 (m,

—CH—);
|
O—

4.5 (q, —CH₂CH₃); 3.5 (m,N—CH₂); 3.2 (s, (CH₃)₂N—CO); 3.0 (s, (CH₃)₂N—CH₂); 2.9 (m, —CH₂CO—); 1.5 (t, —CH₂CH₃).

The mixture of the ester and amide of the gamma-dimethylamino beta-hydroxy butyric acid was dissolved in water and the solution pH brought to 13 with NaOH. The solution was kept in these hydrolysis conditions for 4 hours at 55° C. Subsequently, the solution was eluted on a weakly acid AMBERLITE IRC 50 resin activated in the H⁺ form in order to remove the sodium ions. The collected fractions were lyophilized thus giving a residue consisting of L-norcarnitine.

T.L.C. CHCl₃—MetOH—IsoprOH—H₂O—AcOH (60-40-10-15-15).

$R_F$=0.3[α]= −23 (C=1H₂O).

NMR D₂O 4.5 (IH, m-CH—);
O 3.2 (2H, m, N—CH₂); 2.9 (6H, s, (CH₃)₂N—); 2.4 (2H, d, —CH₂COOH).

What is claimed is:

1. Process for preparing L-norcarnitine

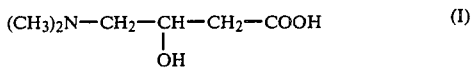

according to the following reaction scheme:

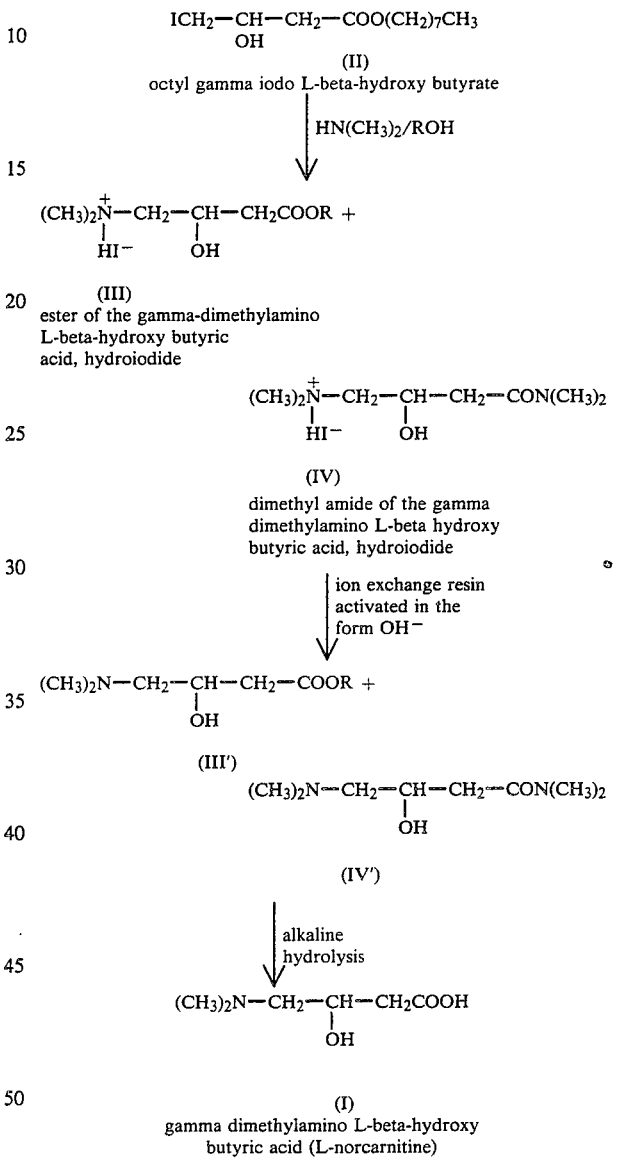

comprising the steps of:
(a) reacting a solution of octyl gamma iodo L-beta hydroxy butyrate (II) in a lower alkanol ROH wherein R is lower alkyl with a solution of dimethylamine in the same lower alkanol with molar ratio from 1:2 to 1:4, keeping the reaction mixture under stirring at 25°–35° C. for 15–24 hours, thereby obtaining a mixture of the hydroiodides of the ester (III) and dimethylamide (IV) of the gamma-dimethylamino-L-beta-hydroxy-butyric acid;
(b) concentrating under vacuum the mixture of step (a), taking up with water the residue and purifying the mixture thus obtained by extraction with a water-immiscible organic solvent, eluting on a weakly basic ion exchange resin activated in the OH⁻ form in order to remove the iodide ion, thereby obtaining a mixture of ester (III') and dimethylamide (IV') of the gamma-dimethylamino L-beta-hydroxy-butyric acid which are not isolated;

(c) hydrolyzing the mixture of the ester (III') and amide (IV') in alkaline aqueous environment at pH 11-13 at 40°-60° C. in about 4 to 8 hours, thereby obtaining L-norcarnitine (I); and (d) purifying the L-norcarnitine thus obtained by removal of the cations via elution on a weakly acid ion exchange resin activated in the H⁺ form.

* * * * *